United States Patent
Rice et al.

(10) Patent No.: US 12,420,007 B2
(45) Date of Patent: Sep. 23, 2025

(54) LOW PROFILE OFF-LOADING FLUID AND PRESSURE CONDUIT

(71) Applicant: KCI Manufacturing Unlimited Company, Westmeath (IE)

(72) Inventors: Justin Rice, Denver, CO (US); James K. Seddon, Wimborne (GB); Benjamin A. Pratt, San Antonio, TX (US); Andrew Neylon, San Antonio, TX (US); John Kennedy, San Antonio, TX (US); Victor Clarke, San Antonio, TX (US)

(73) Assignee: KCI Manufacturing Unlimited Company, Westmeath (IE)

( * ) Notice: Subject to any disclaimer, the term of this patent is extended or adjusted under 35 U.S.C. 154(b) by 172 days.

(21) Appl. No.: 18/035,972

(22) PCT Filed: Oct. 20, 2021

(86) PCT No.: PCT/IB2021/059671
§ 371 (c)(1),
(2) Date: May 9, 2023

(87) PCT Pub. No.: WO2022/101716
PCT Pub. Date: May 19, 2022

(65) Prior Publication Data
US 2023/0405211 A1    Dec. 21, 2023

Related U.S. Application Data

(60) Provisional application No. 63/112,252, filed on Nov. 11, 2020.

(51) Int. Cl.
*A61M 1/00* (2006.01)

(52) U.S. Cl.
CPC .............. *A61M 1/913* (2021.05); *A61M 1/92* (2021.05); *A61M 2207/00* (2013.01)

(58) Field of Classification Search
CPC .................. A61F 13/05; A61F 13/0223; A61F 2013/00536; A61F 2013/00174;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion corresponding to International Patent Application No. PCT/IB2021/059671, Mailed Oct. 3, 2022.
(Continued)

*Primary Examiner* — Nicholas J. Weiss
*Assistant Examiner* — Seth Han

(57) ABSTRACT

An apparatus for managing fluid from a tissue site may include a first layer and a second layer. The first layer may comprise a first end, a second end, a first surface, a thickness between the first surface and the second surface, a first fluid pathway disposed in the first surface, and a second fluid pathway disposed in the first surface. The first fluid pathway and the second fluid pathway can extend from the first end to the second end. The second layer may have a first end, a second end, a first surface, and a second surface. The second surface of the second layer can be coupled to the first surface of the first layer.

19 Claims, 7 Drawing Sheets

(58) Field of Classification Search
CPC ........ A61M 1/913; A61M 1/915; A61M 1/92;
A61M 1/74
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,801,685 B2 * | 8/2014 | Armstrong ............. A61F 13/05 604/319 |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2010/0324516 A1 * | 12/2010 | Braga ............... A61F 13/00 604/378 |
| 2011/0184362 A1 * | 7/2011 | Croizat ............... A61M 1/915 604/319 |
| 2012/0109083 A1 * | 5/2012 | Coulthard ............... A61F 13/05 604/319 |
| 2013/0144230 A1 | 6/2013 | Wu et al. |
| 2014/0163491 A1 | 6/2014 | Schuessler et al. |
| 2015/0080788 A1 | 3/2015 | Blott et al. |
| 2015/0141941 A1 * | 5/2015 | Allen ............... A61F 13/022 604/319 |
| 2016/0106892 A1 * | 4/2016 | Hartwell ............... A61P 17/02 604/304 |
| 2019/0091388 A1 * | 3/2019 | Locke ............... A61M 1/915 |
| 2019/0117861 A1 * | 4/2019 | Locke ............... A61F 13/05 |
| 2020/0038250 A1 | 2/2020 | Edwards et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |

(56) References Cited

FOREIGN PATENT DOCUMENTS

| | | |
|---|---|---|
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ? uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

* cited by examiner

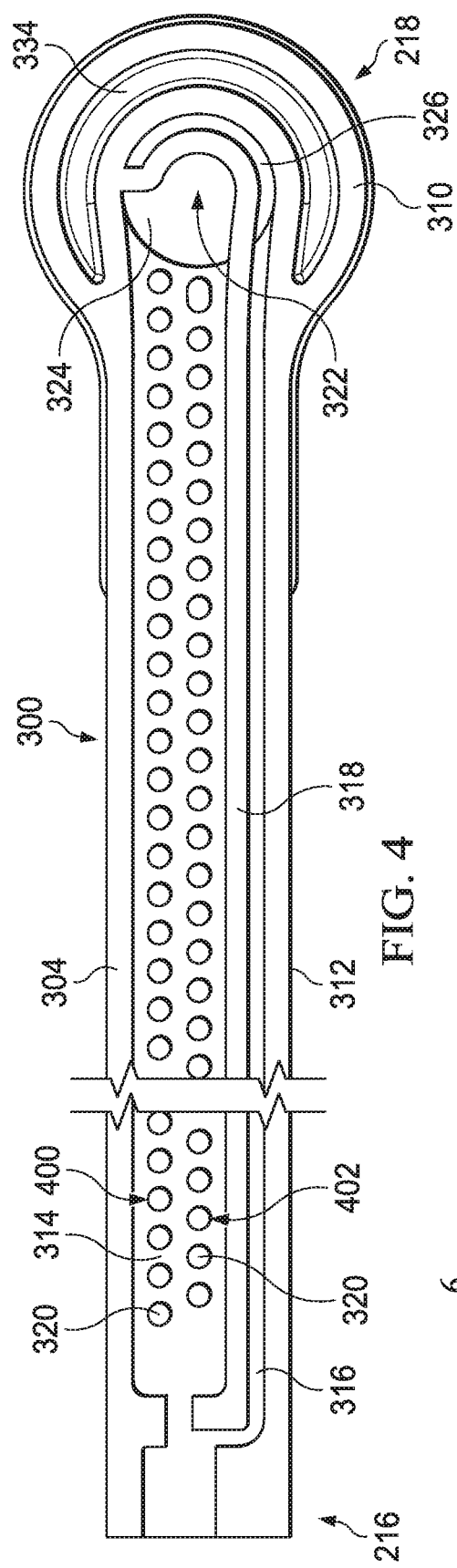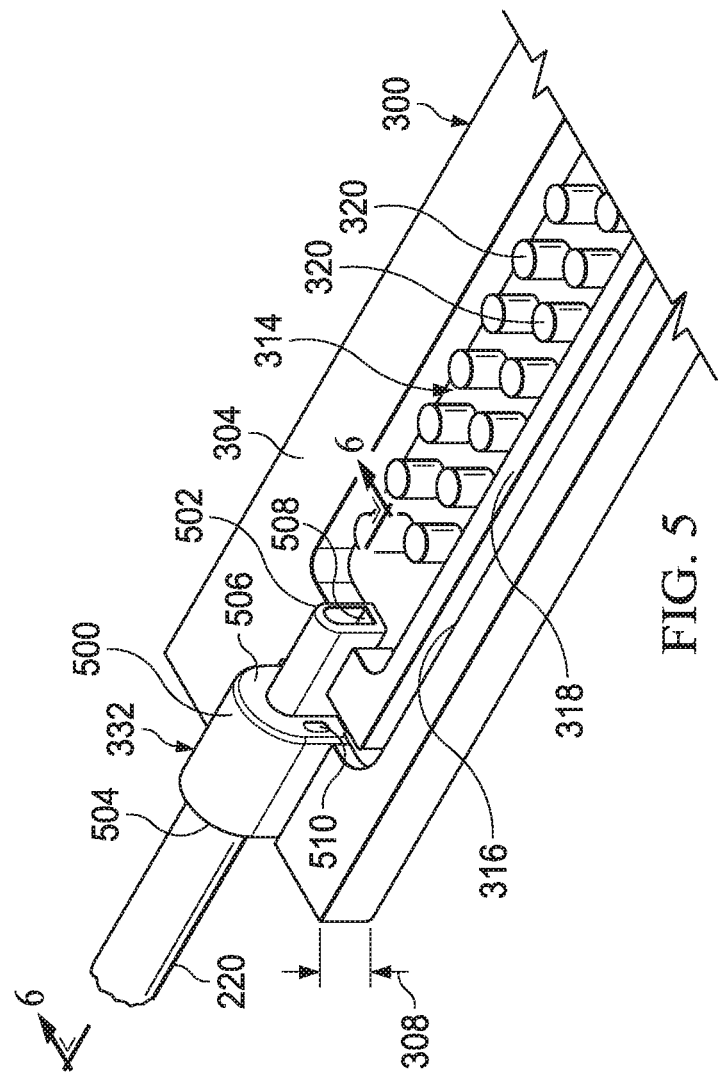

LOW PROFILE OFF-LOADING FLUID AND PRESSURE CONDUIT

CROSS-REFERENCE TO RELATED APPLICATIONS

This application claims the benefit of priority to U.S. Provisional Application No. 63/112,252, filed on Nov. 11, 2020, which is incorporated herein by reference in its entirety.

TECHNICAL FIELD

The invention set forth in the appended claims relates generally to tissue treatment systems and more particularly, but without limitation, to apparatuses and methods for providing negative-pressure therapy and instillation therapy.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions or saline over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, an apparatus for managing fluid from a tissue site may comprise a first layer and a second layer. The first layer can have a first end, a second end, a first surface, a second surface, and a thickness between the first surface and the second surface. In some embodiments, the first layer can comprise a foam. In some embodiments, the first layer can also comprise a first fluid pathway and a second fluid pathway. The first fluid pathway can be disposed in the first surface of the first layer and extend from the first end to the second end. The second fluid pathway can be disposed in the first surface of the first layer and extend from the first end to the second end. In some embodiments, the second layer can have a first end, a second end, a first surface, and a second surface. In some embodiments, the second surface of the second layer can be coupled to the first surface of the first layer.

Alternatively, other example embodiments of an apparatus for managing fluid from a tissue site may comprise a bridge and a cover layer. The bridge can have a first end configured to be fluidly coupled to a conduit and a second end configured to be fluidly coupled to a tissue interface. The bridge can also have an inner surface, an outer surface, and a thickness between the inner surface and the outer surface. In some embodiments, the bridge can include a first lumen formed on the inner surface and along a length of the bridge and a second lumen formed on the inner surface and along the length of the bridge. The first lumen can comprise a plurality of features projecting into the first lumen. The bridge can also include a barrier formed along the length of the bridge and configured to fluidly isolate the first lumen from the second lumen. The cover layer can have a first end, a second end, an inner surface, and an outer surface. The inner surface of the cover layer can be coupled to the inner surface of the bridge and cover the first lumen and the second lumen. In some embodiments, the bridge can include a first aperture and a second aperture. The first aperture and the second aperture can be disposed in the second end of the bridge. The first aperture can be fluidly coupled to the first lumen and the second aperture can be fluidly coupled to the second lumen.

A method of manufacturing an apparatus for managing fluid from a tissue site is also described herein, wherein some example embodiments include providing a first layer. The first layer can comprise a foam having a first surface and a second surface opposite the first surface. Providing a first layer can include forming a first fluid channel on the first surface of the first layer, forming a second fluid channel on the first surface of the first layer, forming a barrier on the first surface of the first layer, disposing a first aperture in the first layer, and disposing a second aperture in the first layer. In some embodiments, the first fluid channel can include a plurality of features extending from the first surface into the first fluid channel. In some embodiments, the barrier can be configured to fluidly isolate the first fluid channel from the second fluid channel. In some embodiments, the first aperture can be configured to be fluidly coupled to the first fluid channel and the second aperture can be configured to be fluidly coupled to the second fluid channel. In some embodiments, the barrier can fluidly isolate the first aperture from the second aperture.

The method can further include providing a second layer. The second layer can comprise a polymeric film having an outer surface and an inner surface. Providing a second layer may include coupling the inner surface of the second layer to the first surface of the first layer. In some embodiments, the method may further include fluidly coupling at least one conduit to the first fluid channel and the second fluid channel.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 4 is a plan view of a first layer of the dressing interface of FIG. 3, illustrating additional details that may be associated with some embodiments;

FIG. 5 is a perspective view of a portion of the first layer and a connector of FIG. 3, illustrating additional details that may be associated with some embodiments;

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
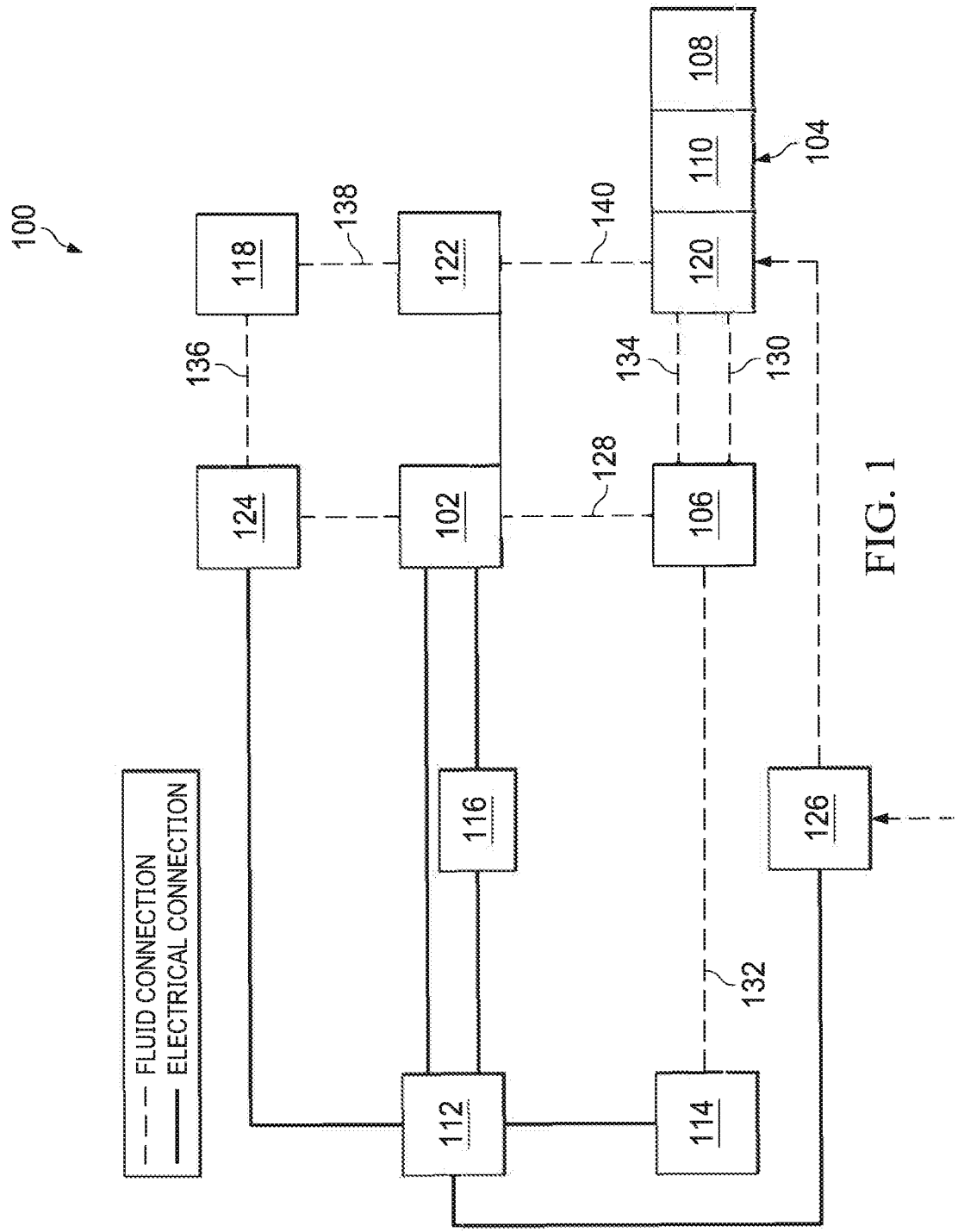
FIG. 1 is a functional block diagram of an example embodiment of a therapy system that can provide negative-pressure treatment and instillation treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 102, and one or more distribution components. A distribution component is preferably detachable and may be disposable, reusable, or recyclable. A dressing, such as a dressing 104, and a fluid container, such as a container 106, are examples of distribution components that may be associated with some examples of the therapy system 100. As illustrated in the example of FIG. 1, the dressing 104 may comprise or consist essentially of a tissue interface 108, a cover 110, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface 120 may facilitate coupling a fluid conductor to the dressing 104. For example, such a dressing interface may be a SENSA-T.R.A.C.™ Pad available from Kinetic Concepts, Inc. of San Antonio, Texas.

The therapy system 100 may also include a regulator or controller, such as a controller 112. Additionally, the therapy system 100 may include sensors to measure operating parameters and provide feedback signals to the controller 112 indicative of the operating parameters. As illustrated in FIG. 1, for example, the therapy system 100 may include a first sensor 114 and a second sensor 116 coupled to the controller 112.

In general, components of the therapy system 100 may be coupled directly or indirectly. For example, the negative-pressure source 102 may be directly coupled to the container 106 and may be indirectly coupled to the dressing 104 through the container 106. Coupling may include fluid, mechanical, thermal, electrical, or chemical coupling (such as a chemical bond), or some combination of coupling in some contexts. For example, the negative-pressure source 102 may be electrically coupled to the controller 112 and may be fluidly coupled to one or more distribution components to provide a fluid path to a tissue site.

In some embodiments, components may also be coupled by virtue of physical proximity, being integral to a single structure, or being formed from the same piece of material. Coupling may also include mechanical, thermal, electrical, or chemical coupling (such as a chemical bond) in some contexts. For example, a tube may mechanically and fluidly couple the dressing 104 to the container 106. In general, components of the therapy system 100 may be coupled directly or indirectly. For example, the negative-pressure source 102 may be directly coupled to the container 106 and may be indirectly coupled to the dressing 104 through the container 106 by a conduit 128 and a negative-pressure delivery conduit 130. The negative-pressure source 102 may be electrically coupled to the controller 112 and may be fluidly coupled to one or more distribution components to provide a fluid path to a tissue site. The first sensor 114 may be fluidly coupled to the dressing 104 directly or indirectly by a conduit 132 and a pressure-sensing conduit 134.

A negative-pressure supply, such as the negative-pressure source 102, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 102 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 106 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 112, may be a microprocessor or computer programmed to operate one or more components of the therapy system 100, such as the negative-pressure source 102. In some embodiments, for example, the controller 112 may be a microcontroller, which generally comprises an integrated circuit containing a processor core and a memory programmed to directly or indirectly control one or more operating parameters of the therapy system 100. Operating parameters may include the power applied to the negative-pressure source 102, the pressure generated by the negative-pressure source 102, or the pressure distributed to the tissue interface 108, for example. The controller 112 is also preferably configured to receive one or more input signals, such as a feedback signal, and programmed to modify one or more operating parameters based on the input signals.

Sensors, such as the first sensor 114 and the second sensor 116, are generally known in the art as any apparatus operable to detect or measure a physical phenomenon or property, and generally provide a signal indicative of the phenomenon or property that is detected or measured. For example, the first sensor 114 and the second sensor 116 may be configured to measure one or more operating parameters of the therapy system 100. In some embodiments, the first sensor 114 may be a transducer configured to measure pressure in a pneumatic pathway and convert the measurement to a signal indicative of the pressure measured. In some embodiments, for example, the first sensor 114 may be a piezo-resistive strain gauge. The second sensor 116 may optionally measure operating parameters of the negative-pressure source 102, such as a voltage or current, in some embodiments. Preferably, the signals from the first sensor 114 and the second sensor 116 are suitable as an input signal to the controller 112, but some signal conditioning may be appropriate in some embodiments. For example, the signal may need to be filtered or amplified before it can be processed by the controller 112. Typically, the signal is an electrical signal, but may be represented in other forms, such as an optical signal.

The tissue interface 108 can be generally adapted to partially or fully contact a tissue site. The tissue interface 108 may take many forms, and may have many sizes, shapes, or thicknesses, depending on a variety of factors, such as the type of treatment being implemented or the nature and size of a tissue site. For example, the size and shape of the tissue interface 108 may be adapted to the contours of deep and irregular shaped tissue sites. Any or all of the surfaces of the tissue interface 108 may have an uneven, coarse, or jagged profile.

In some embodiments, the tissue interface 108 may comprise or consist essentially of a manifold. A manifold in this context may comprise or consist essentially of a means for collecting or distributing fluid across the tissue interface 108 under pressure. For example, a manifold may be adapted to receive negative pressure from a source and distribute negative pressure through multiple apertures across the tissue interface 108, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 108 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 108 may also vary according to needs of a prescribed therapy. For example, the tensile strength of foam may be increased for instillation of topical treatment solutions. The 25% compression load deflection of the tissue interface 108 may be at least 0.35 pounds per square inch, and the 65% compression load deflection may be at least 0.43 pounds per square inch. In some embodiments, the tensile strength of the tissue interface 108 may be at least 10 pounds per square inch. The tissue interface 108 may have a tear strength of at least 2.5 pounds per inch. In some embodiments, the tissue interface may be foam comprised of polyols such as polyester or polyether, isocyanate such as toluene diisocyanate, and polymerization modifiers such as amines and tin compounds. In some examples, the tissue interface 108 may be reticulated polyurethane foam such as found in GRANUFOAM™ dressing or V.A.C. VERAFLO™ dressing, both available from Kinetic Concepts, Inc. of San Antonio, Texas.

The thickness of the tissue interface 108 may also vary according to needs of a prescribed therapy. For example, the thickness of the tissue interface may be decreased to reduce tension on peripheral tissue. The thickness of the tissue interface 108 can also affect the conformability of the tissue interface 108. In some embodiments, a thickness in a range of about 5 millimeters to 10 millimeters may be suitable.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic material that may be suitable is a polyvinyl alcohol, open-cell foam such as V.A.C. WHITEFOAM™ dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 110 may provide a bacterial barrier and protection from physical trauma. The cover 110 may also be constructed from a material that can reduce evaporative losses and provide a fluid seal between two components or two environments, such as between a therapeutic environment and a local external environment. The cover 110 may comprise or consist of, for example, an elastomeric film or membrane that can provide a seal adequate to maintain a negative pressure at a tissue site for a given negative-pressure source. The cover 110 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 110 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 110 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inspire 2327 polyurethane films, commercially available from Expopack Advanced Coatings, Wrexham, United Kingdom. In some embodiments, the cover 110 may comprise INSPIRE 2301 having an MVTR (upright cup technique) of 2600 $g/m^2/24$ hours and a thickness of about 30 microns.

An attachment device may be used to attach the cover 110 to an attachment surface, such as undamaged epidermis, a gasket, or another cover. The attachment device may take many forms. For example, an attachment device may be a medically-acceptable, pressure-sensitive adhesive configured to bond the cover 110 to epidermis around a tissue site. In some embodiments, for example, some or all of the cover 110 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The therapy system 100 may also include a source of instillation solution, such as a solution source 118. The solution source 118 may be fluidly coupled to the dressing 104 and, in some embodiments, the solution source 118 may be fluidly coupled to a positive-pressure source, such as an instillation pump 124. A regulator, such as an instillation regulator 122, may also be fluidly coupled to the solution source 118 and the dressing 104 to ensure proper dosage of instillation solution (e.g. saline) to a tissue site. For example, the instillation regulator 122 may comprise a piston that can be pneumatically actuated by the negative-pressure source 102 to draw instillation solution from the solution source during a negative-pressure interval and to instill the solution to a dressing during a venting interval. Additionally or alternatively, the controller 112 may be coupled to the negative-pressure source 102, the instillation pump 124, or both, to control dosage of instillation solution to a tissue site. In some embodiments, the instillation regulator 122 may also be fluidly coupled to the negative-pressure source 102 through the dressing 104, as illustrated in the example of FIG. 1.

The instillation pump 124 may be fluidly coupled to the solution source 118, as illustrated in the example embodiment of FIG. 1. The instillation pump 124 may also be fluidly coupled to the negative-pressure source 102. In some embodiments, the instillation pump 124 may be directly coupled to the negative-pressure source 102. In other embodiments, the instillation pump 124 may be indirectly coupled to the negative-pressure source 102 through other distribution components. For example, the instillation pump 124 may be fluidly coupled to the negative-pressure source 102 through the dressing 104. Additionally, the instillation pump 124 may be coupled indirectly to the dressing 104 through the solution source 118 and the instillation regulator 122 by a conduit 136, a conduit 138, and a conduit 140. Alternatively, the instillation pump 124 may be coupled indirectly to the dressing 104 through a second dressing interface coupled to the dressing 104.

The solution source 118 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies a position in a fluid path relatively closer to a source of negative pressure or further away from a source of positive pressure. Conversely, the term "upstream" implies a position relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

In some embodiments, the controller 112 may receive and process data from one or more sensors, such as the first sensor 114. The controller 112 may also control the operation of one or more components of the therapy system 100 to manage the pressure delivered to the tissue interface 108. In some embodiments, controller 112 may include an input for receiving a desired target pressure and may be programmed for processing data relating to the setting and inputting of the target pressure to be applied to the tissue interface 108. In some example embodiments, the target pressure may be a fixed pressure value set by an operator as the target negative pressure desired for therapy at a tissue site and then provided as input to the controller 112. The target pressure may vary from tissue site to tissue site based on the type of tissue forming a tissue site, the type of injury or wound (if any), the medical condition of the patient, and the preference of the attending physician. After selecting a desired target pressure, the controller 112 can operate the negative-pressure source 102 in one or more control modes based on the target pressure and may receive feedback from one or more sensors to maintain the target pressure at the tissue interface 108.

The therapy system 100 may also comprise a flow regulator such as, for example, a regulator 126 fluidly coupled to a source of ambient air to provide a controlled or managed flow of ambient air to the sealed therapeutic environment provided by the dressing 104 and ultimately the tissue site. In some embodiments, the regulator 126 may control the flow of ambient air to purge fluids and exudates from the sealed therapeutic environment. In some embodiments, the regulator 126 may be fluidly coupled to the tissue interface 108 through the dressing interface 120. The regulator 126 may be configured to fluidly couple the tissue interface 108 to a source of ambient air. In some embodiments, the regulator 126 may be disposed within the therapy system 100 rather than being proximate to the dressing 104 so that the air flowing through the regulator 126 is less susceptible to accidental blockage during use. In some embodiments, the regulator 126 may be positioned proximate the container 106 and/or proximate a source of ambient air, where the regulator 126 is less likely to be blocked during usage.

Some therapy systems require continuous monitoring, maintenance, and support to ensure the leaks and blockages do not go undiscovered and negatively affect treatment. For example, a leak or blockage may completely or partially prevent negative pressure from being delivered to the tissue site. Additionally, some dressings may be difficult to accurately align and apply at a tissue site. For example, it may be difficult for a clinician to align a dressing with an aperture in a cover. Improper application and alignment of the dressing may result in leaks that prevent negative pressure from being delivered to the tissue site. Further, the dressing may need to be replaced if it is not applied accurately, resulting in waste. Repeated removal or relocation of the dressing due to misalignment of the dressing can cause patient discomfort, disrupt treatment, and potentially damage the cover or healthy tissue surrounding the tissue site.

These limitations and others may be addressed by the therapy system 100, which can provide negative pressure therapy. In some embodiments, the therapy system 100 may also provide instillation therapy. In some embodiments, the therapy system 100 may also continuously monitor for leaks and blockages, reducing treatment maintenance and ongoing therapy support time required by a clinician. For example, the dressing interface 120 may include one or more pressure-sensing pathways to monitor pressure at the tissue site. In some embodiments, the therapy system 100 may include sensors and alarms to indicate if a leak or blockage has occurred. In some embodiments, the dressing interface 120 may also include multiple fluid pathways to prevent blockages and maintain an open pathway for negative pressure treatment and/or instillation therapy.

In some embodiments, the dressing 104 of the therapy system 100 can be easily aligned and applied to a tissue site to prevent leaks. For example, the dressing interface 120 of the therapy system 100 may improve fluid coupling across the cover 110, reducing instances of misalignment between an aperture in the cover 110 and the dressing interface 120. A properly aligned dressing can also prevent patient discomfort from having to reposition a misaligned dressing and prevent waste from having to replace the misaligned dressing entirely.

Figure 2:
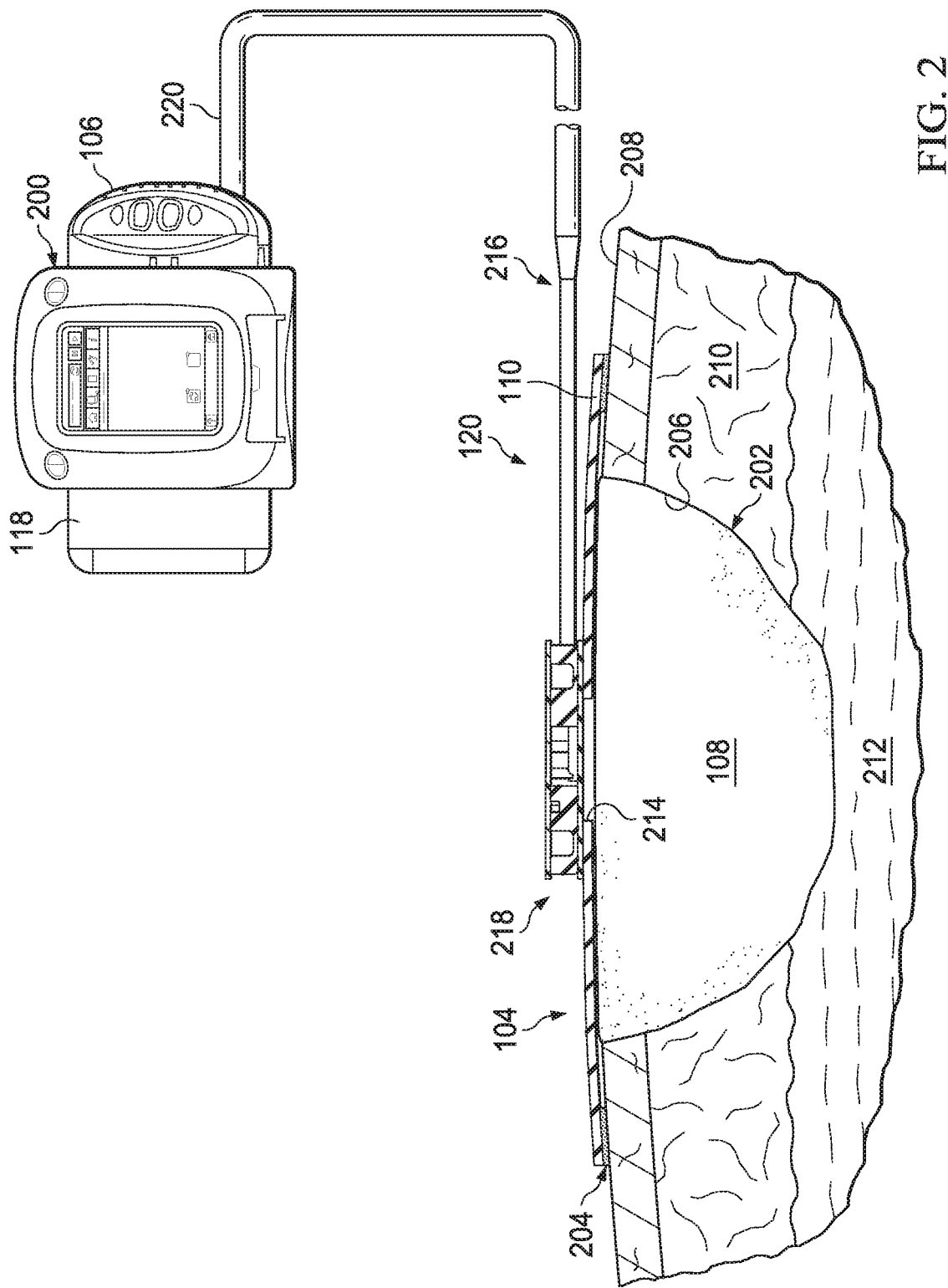
FIG. 2 is a schematic diagram of an example embodiment of the therapy system of FIG. 1, illustrating additional details that may be associated with some embodiments.

FIG. 2 is a schematic diagram of an example embodiment of the therapy system 100, illustrating additional details that may be associated with some embodiments. Some components of the therapy system 100 may be housed within or used in conjunction with other components, such as processing units, alarm indicators, memory, databases, software, display devices, or user interfaces that further facilitate therapy. For example, in some embodiments, the negative-pressure source 102 may be combined with the controller 112, the solution source 118, and other components into a therapy unit, such as a therapy unit 200. The therapy unit 200 may be, for example, a V.A.C.ULTA™ Therapy Unit available from Kinetic Concepts, Inc. of San Antonio, Texas.

In operation, the tissue interface 108 may be placed within, over, on, or otherwise proximate a tissue site, such as tissue site 202. If the tissue site is a wound, for example, the tissue interface 108 may partially or completely fill the wound, or it may be placed over the wound. In the example of FIG. 2, the tissue site 202 extends through an epidermis 208, or generally skin, and a dermis 210 reaching into a hypodermis, or a subcutaneous tissue 212. The therapy system 100 may be used to treat a wound of any depth, as well as many different types of wounds, including open wounds, incisions, or other tissue sites. Treatment of the tissue site 202 may include removal of fluids originating from the tissue site 202, such as exudates or ascites, or fluids instilled into the dressing to cleanse or treat the tissue site 202, such as antimicrobial solutions.

The cover 110 may be placed over the tissue interface 108 and an attachment device 204 can seal the cover 110 to an attachment surface near the tissue site 202. For example, the cover 110 may be sealed to undamaged epidermis peripheral to a tissue site. Thus, the dressing 104 can provide a sealed therapeutic environment proximate to the tissue site 202, substantially isolated from the external environment, and the therapy unit 200 can reduce the pressure in the sealed therapeutic environment. Negative pressure applied across the tissue site 202 through the tissue interface 108 in the sealed therapeutic environment can induce macrostrain and microstrain in the tissue site 202. Negative pressure can also remove exudates and other fluids from the tissue site 202, which can be collected in the container 106.

In some embodiments, the cover 110 may have one or more openings, apertures, or holes. For example, the cover may have a hole 214 disposed in the cover 110. In some embodiments, the therapy unit 200 may be fluidly coupled to the dressing 104 by the dressing interface 120. The dressing interface 120 may be coupled to the cover 110 adjacent to the hole 214 to fluidly couple the therapy unit 200 to the tissue interface 108.

In some embodiments, the dressing interface 120 may comprise a first end 216 configured to be fluidly coupled to a tube or a conduit, such as a conduit 220, and a second end 218 configured to be fluidly coupled to the tissue interface 108. Generally, the dressing interface 120 may be substantially flat and flexible, but also compressible without occluding or blocking the fluid pathway between the conduit 220 and the tissue interface 108.

Figure 3:
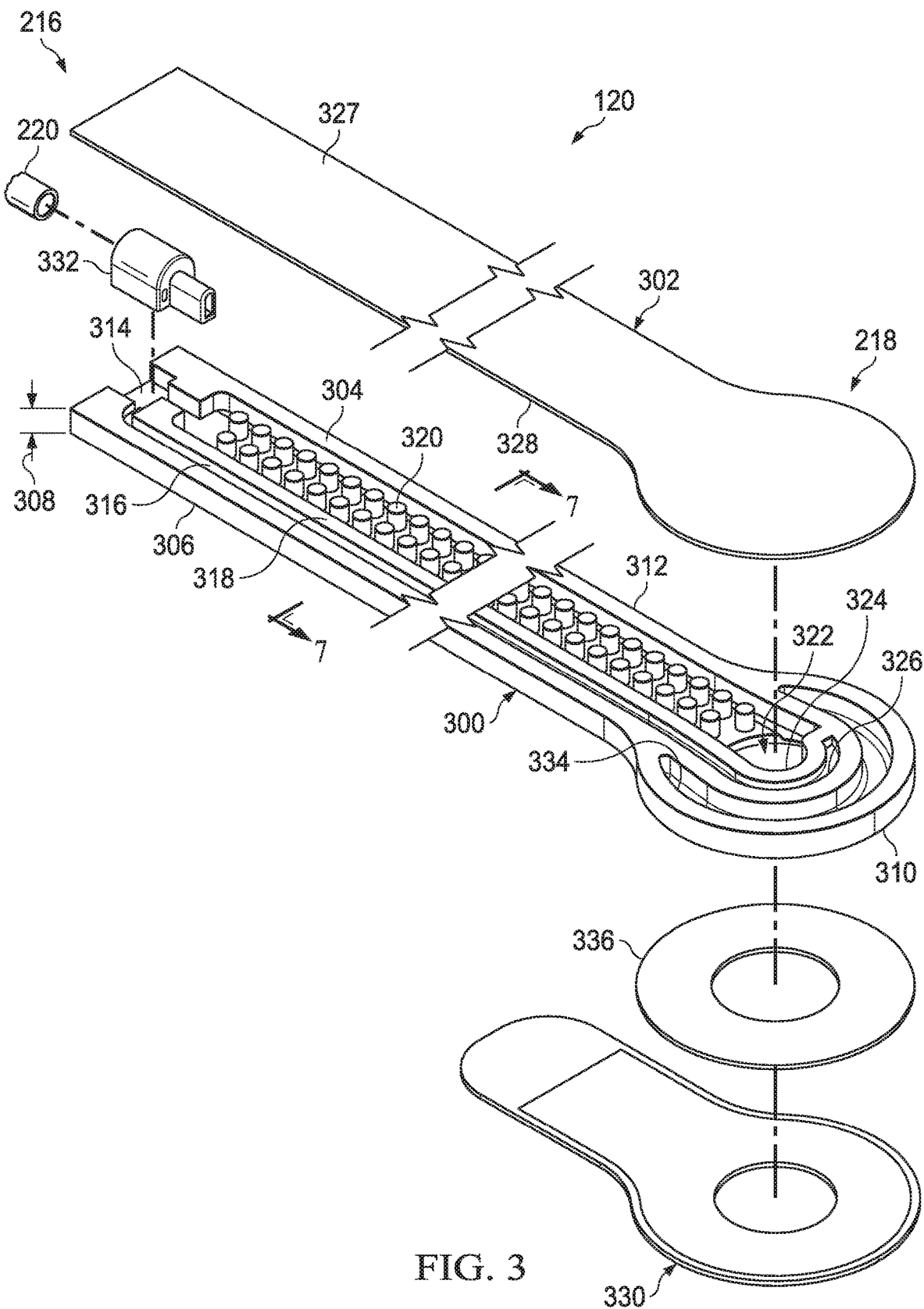
FIG. 3 is an assembly view of a dressing interface of FIG. 2, illustrating additional details that may be associated with some embodiments.

FIG. 3 is an assembly view of the dressing interface 120 of FIG. 2, illustrating additional details that may be associated with some embodiments. In some embodiments, the dressing interface 120 may comprise a bridge, such as a first layer 300, and a cover layer, such as a second layer 302. The first layer 300 may extend from the first end 216 to the second end 218. The first layer 300 may comprise an inner surface, such as a first surface 304; an outer surface, such as a second surface 306; and a thickness 308 between the first surface 304 and the second surface 306. In some embodiments, the thickness 308 of the first layer 300 may be between about 5 mm and about 10 mm.

In some embodiments, the first layer 300 may comprise an applicator 310 and an elongate portion 312. The applicator 310 may be positioned at the second end 218 and configured to be fluidly coupled to the tissue interface 108. The applicator 310 may be a circular, oval, elliptical, or other rounded shape. In some embodiments, the applicator 310 may have an effective diameter between about 20 and about 60 mm. In other embodiments, the applicator 310 may have a polygonal, square, rectangular, triangular, or amorphous shape.

The elongate portion 312 may extend from the first end 216 of the dressing interface 120 to the applicator 310. In some embodiments, the applicator 310 and the elongate portion 312 may be formed as a single device to form the first layer 300. In other embodiments, the applicator 310 and the elongate portion 312 may be separate components coupled together to form the first layer 300.

The elongate portion 312 can comprise a generally rectangular body having a length greater than its width. In some embodiments, the length of the elongate portion 312 may be determined by the desired treatment. For example, the length of the elongate portion 312 may be longer for treating a patient's foot than for treating a patient's knee. In some embodiments, the length of the elongate portion 312 may be between about 130 and about 900 mm. In some embodiments, the length of the elongate portion 312 may be ten times the width of the elongate portion 312. In some embodiments, the width of the elongate portion 312 may be between about 20 and about 30 mm.

In some embodiments, the width of the elongate portion 312 may be determined by the amount of fluid to be removed from the tissue site 202. For example, the width of the elongate portion 312 may be smaller when removing lower volumes of fluid having a low viscosity. In other embodiments, the width of the elongate portion 312 may be greater to remove a higher volume of fluid having a high viscosity. In some embodiments, the width of the elongate portion 312 may be less than the effective diameter of the applicator 310. In other embodiments, the width of the elongate portion 312 may be equal to or greater than the effective diameter of the applicator 310. A center of the width of the elongate portion 312 may be aligned with a diameter of the applicator 310. In other embodiments, the center of the width of the elongate portion 312 may be offset from the diameter of the applicator 310.

In some embodiments, the first layer 300 may have a length extending from the first end 216 to the second end 218 of the dressing interface 120. In some embodiments, the length of the first layer 300 may be substantially equal to the length of the elongate portion 312 plus the diameter of the applicator 310. In some embodiments, the length of the first layer 300 may preferably be between about 50 mm and about 150 mm.

In some embodiments, the first layer 300 may comprise a first lumen, such as a first fluid pathway 314, and a second lumen, such as a second fluid pathway 316, disposed in the first surface 304 of the first layer 300. For example, the first fluid pathway 314 and the second fluid pathway 316 may extend into a portion of the thickness 308 of the first layer 300 from the first surface 304 toward the second surface 306. The first fluid pathway 314 and the second fluid pathway 316 may each extend along the length of the elongate portion 312 to the applicator 310. In some embodiments, the first fluid pathway 314 of the first layer 300 may comprise a plurality of features 320 projecting into the first fluid pathway 314. The plurality of features 320 may have a volumetric shape that is any one of a hemispherical, conical, cylindrical, rectangular, ovoid, or geodesic shape. In some embodiments, the first fluid pathway 314 may be configured to deliver negative pressure to the tissue site 202 and the second fluid pathway 316 may be configured to sense pressure at the tissue site 202.

In some embodiments, the first layer 300 may comprise a barrier, such as a wall 318, extending along the length of the elongate portion 312 toward the applicator 310. The wall 318 may fluidly isolate the first fluid pathway 314 from the second fluid pathway 316. In some embodiments, the wall 318 may extend into at least a portion of the applicator 310.

In some embodiments, the first layer 300 may comprise at least one opening, such as an opening 322, disposed in the applicator 310 and extending through the thickness 308 of the first layer 300 from the first surface 304 to the second surface 306. The first fluid pathway 314 and the second fluid pathway 316 may be fluidly coupled to the opening 322. In some embodiments, the opening 322 may be circular. In other embodiments, the opening 322 may be a circular, oval, elliptical, polygonal, square, rectangular, triangular, or amorphous shape. In some embodiments, the wall 318 may extend into the opening 322 and divide the opening into at least two portions, such as a first aperture 324 and a second aperture 326. The first fluid pathway 314 may be fluidly coupled to the first aperture 324 of the opening 322 and the second fluid pathway 316 may be fluidly coupled to the second aperture 326 of the opening 322. In some embodiments, the wall 318 may extend into the opening 322 of the applicator 310 and be concentric with the opening 322.

In some embodiments, the applicator 310 of the first layer 300 may comprise a recessed portion 334. The recessed portion 334 may be positioned at least partially around a perimeter of the applicator 310. For example, the recessed portion 334 may be concentric with a portion of the opening 322. In some embodiments, the recessed portion 334 may extend into the thickness 308 of the first layer 300 from the first surface 304 toward the second surface 306. In other embodiments, the recessed portion 334 may extend through the thickness 308 of the first layer 300 from the first surface 304 to the second surface 306.

In some embodiments, the first layer 300 may comprise a foam. For example, the first layer 300 may comprise a closed-cell foam or other suitable non-porous material. For example, the first layer 300 may comprise or consist essentially of silicone, polyurethane (PU), or ethylene vinyl acetate (EVA). The structure of these closed-cell foams can provide a surface that interacts little, if any, with biological tissues and fluids, providing a surface that may encourage the free flow of liquids and low adherence, which can be particularly advantageous for many applications. In some embodiments, the closed-cell foam may have a density of about 4 lb/ft$^3$ to about 20 lb/ft$^3$. In other embodiments, the first layer 300 may comprise flexible polyurethane resins, flexible silicones, and/or flexible plasticized polyvinyl chloride (PVC). In still other embodiments, the first layer 300 comprise an open-cell foam. The surface of the open-cell foam may be sealed to create a non-porous first layer 300. In other embodiments, the first layer 300 may be formed by injection molding or compression molding.

In some embodiments, the dressing interface 120 may include an attachment device 336. The attachment device 336 can be coupled to the second surface 306 of the first layer 300. In some embodiments, the attachment device 336 may be coupled to the applicator 310 on the second surface 306 of the first layer 300 and be configured to surround the opening 322 of the applicator 310. For example, the adhesive ring may be a double-sided pressure sensitive adhesive ring. In some embodiments, the attachment device 336 may be configured to couple the dressing interface 120 to the cover 110 of the dressing 104 and surround the hole 214 of the cover 110 to create a seal to prevent leakage of negative pressure and fluids. Other example embodiments of the attachment device 336 may include a double-sided tape, paste, hydrocolloid, hydrogel, silicone gel, or organogel.

In some embodiments, the dressing interface 120 can include a release layer 330. The release layer 330 may be removably coupled to the second surface 306 of the first layer 300. In some embodiments, the release layer 330 may be removably coupled to the applicator 310. In some embodiments, the release layer 330 may be removably coupled to the attachment device 336. In some embodiments, the release layer 330 may comprise a film. For example, the release layer 330 may be formed from the same material as the cover 110. The release layer 330 can protect the attachment device 336 prior to the dressing interface 120 being applied to the tissue site 202. For example, during transport and initial handling of the dressing interface 120, the release layer 330 may prevent the adhesive ring from losing moisture, allowing the adhesive ring to maintain its tack prior to use. During application of the dressing interface 120, the release layer 330 can be removed, exposing the adhesive ring for placement of the adhesive ring into contact with the cover 110.

In some embodiments, the second layer 302 may extend from the first end 216 to the second end 218 of the dressing interface 120. The second layer 302 may also be configured to be positioned adjacent the first surface 304 of the first layer 300. For example, the second layer 302 and the first layer 300 may be stacked so that the second layer 302 is in contact with the first layer 300. In some embodiments, the second layer 302 may comprise an outer surface, such as a first surface 327, and an inner surface, such as a second surface 328. In some embodiments, the second surface 328 of the second layer 302 may be coupled to the first surface 304 of the first layer 300 to form a sealed space within the dressing interface 120. The first fluid pathway 314 and the second fluid pathway 616 may be formed within the sealed space between the first layer 300 and the second layer 302. In some embodiments, the first layer 300 and the second layer 302 may each have a periphery extending along a perimeter of the first layer 300 and the second layer 302. The periphery of the first layer 300 may be coupled to the periphery of the second layer 302 to form the sealed space. For example, the periphery of the first layer 300 and the periphery of the second layer 302 may be coupled by welding (RF or ultrasonic), heat sealing, or adhesive bonding such as, for example, acrylics or cured adhesives. One skilled in the art would understand that there are a variety of methods for coupling the first layer 300 to the second layer 302 to form the sealed space within the dressing interface 120.

The area density of the second layer 302 may vary according to a prescribed therapy or application. In some embodiments, an area density of less than 40 grams per square meter may be suitable, and an area density of about 20-30 grams per square meter may be particularly advantageous for some applications.

In some embodiments, the second layer 302 may be a hydrophobic polymer, such as a polyethylene film. The simple and inert structure of polyethylene can provide a surface that interacts little, if any, with biological tissues and fluids, providing a surface that may encourage the free flow of liquids and low adherence, which can be particularly advantageous for many applications. Other suitable polymeric films include polyurethanes, acrylics, polyolefin (such as cyclic olefin copolymers), polyacetates, polyamides, polyesters, copolyesters, PEBAX block copolymers, thermoplastic elastomers, thermoplastic vulcanizates, polyethers, polyvinyl alcohols, polypropylene, polymethylpentene, polycarbonate, styreneics, silicones, fluoropolymers, and acetates. A thickness between about 100 microns and about 250 microns may be suitable for many applications. Films may be clear, colored, or printed. More polar films suitable for laminating to a polyethylene film include polyamide, co-polyesters, ionomers, and acrylics. To aid in the bond between a polyethylene and polar film, tie layers may be used, such as ethylene vinyl acetate, or modified polyurethanes. An ethyl methyl acrylate (EMA) film may also have suitable hydrophobic and welding properties for some configurations. In other embodiments, the second layer 302 may be formed from the same material as the first layer 300. For example, the second layer 302 may comprise a closed-cell foam having a density of about 4 lb/ft³ to about 20 lb/ft³. In some embodiments, the second layer 302 may be transparent.

In some embodiments, a connector 332 may be coupled to the dressing interface 120. In some embodiments, the connector 332 may be coupled to the first end 216 of the dressing interface 120, providing a fluid path from the first fluid pathway 314 and the second fluid pathway 316 to an environment external to the dressing interface 120. For example, the connector 332 may be bonded, thermally bonded, solvent bonded, or ultrasonically welded to the first layer 300 and the second layer 302 at the first end 216 of the dressing interface 120. In some embodiments, the connector 332 may be fitted to the first layer 300 of the dressing interface 120. For example, the connector 332 may be embedded in the first layer 300 to prevent the connector 332 from being pulled out during treatment. In some embodiments, the connector 332 may be bonded to the first layer 300 and the second layer 302 by an adhesive. For example, the adhesive may comprise an ultra-violet, curable adhesive; a pressure-sensitive adhesive; or an epoxy. Bonding the connector 332 to the first layer 300 and the second layer 302 may create a fluid seal separating the first fluid pathway 314 and the second fluid pathway 316.

The conduit 220 may be coupled to the connector 332, and the connector 332 may fluidly couple the conduit 220 to the first fluid pathway 314 and the second fluid pathway 316. In other embodiments, the conduit 220 may be directly coupled to the dressing interface 120. For example, the conduit 220 may be inserted into and sealed to the first end 216 of the dressing interface 120.

FIG. 4 is a plan view of the first layer 300 of the dressing interface 120 of FIG. 3, illustrating additional details that may be associated with some embodiments. In some embodiments, the first fluid pathway 314, the second fluid pathway 316, and the plurality of features 320 may be thermoformed or laser etched onto the first surface 304 of the first layer 300. In some embodiments, the plurality of features 320 may be positioned within the first fluid pathway 314 in at least two rows, such as a first row 400 and a second row 402. The plurality of features 320 may be offset from each other. For example, the plurality of features 320 in the first row 400 may be staggered from the plurality of features 320 in the second row 402. In some embodiments, the plurality of features 320 may create a plurality of flow channels within the first fluid pathway 314. The plurality of flow channels provide fluid pathway redundancy to reduce blockages. For example, the plurality of flow channels created by the plurality of features 320 may maintain an open pathway while also disrupting exudate flow to break up clots and thick exudate within the first fluid pathway 314. In some embodiments, the plurality of features 320 may also prevent the second layer 302 from collapsing into the first fluid pathway 314 and the second fluid pathway 316 of the first layer 300 during treatment. For example, the plurality of features 320 keep the first fluid pathway 314 and the second fluid pathway open if the dressing interface 120 is folded or under compression, such as if a patient is lying on top of the dressing interface 120.

In some embodiments, the wall 318 may be formed between the first fluid pathway 314 and the second fluid pathway 316. The wall 318 may have an exterior surface that is coplanar with the first surface 304 of the first layer 300. In other embodiments, the wall 318 may have a height that is less than the thickness 308 of the first layer 300. In other embodiments, the wall 318 may be a separate component formed or stamped from a sheet of material and then bonded to the first layer 300 between the first fluid pathway 314 and the second fluid pathway 316. The sheet of material forming the wall 318 may be comprised of the same material as the first layer 300.

In some embodiments, a portion of the wall 318 may extend into the applicator 310 and divide the opening 322 into the first aperture 324 and the second aperture 326. The wall 318 may fluidly isolate the first aperture 324 from the second aperture 326. In some embodiments, the portion of the wall 318 extending into the applicator 310 may be concentric with at least a portion of the opening 322. For example, the second aperture 326 may comprise a portion of a perimeter of the opening 322 and be concentric with at least a portion of the first aperture 324. In some embodiments, the first aperture 324 may be larger than the second aperture 326. In some embodiments, the first aperture 324 may be fluidly coupled to the first fluid pathway 314 and the second aperture 326 may be fluidly coupled to the second fluid pathway 316.

In some embodiments, the opening 322 may be formed by cutting, punching, melting, laser cutting, or otherwise removing material from the applicator 310 of the first layer 300. In some embodiments, the opening 322 may be formed after forming the first fluid pathway 314, the second fluid pathway 316, and the wall 318. For example, the opening 322 may be formed by removing a portion of material from the applicator 310 on a first side of the wall 318, forming the first aperture 324, and removing a portion of material from the applicator 310 on a second side of the wall 318, forming the second aperture 326.

In some embodiments, the recessed portion 334 may be formed by thermoforming, laser etching, or computer numerical control (CNC) milling a portion of the perimeter of the applicator 310 on the first surface 304 of the first layer 300. In some embodiments, the recessed portion 334 may extend from the first surface 304 into a portion of the applicator 310 of the first layer 300. In other embodiments, the recessed portion 334 may extend from the first surface 304 to the second surface 306 of the first layer 300. In some embodiments, the recessed portion 334 may aid with accurate placement of the dressing interface at the tissue site 202. For example, the recessed portion 334 makes the applicator 310 more flexible, aiding the user and patient with proper placement of the applicator 310 at the tissue site 202. Additionally, or alternatively, the recessed portion 334 may aid with manufacturing and leak testing of the dressing interface 120. For example, the recessed portion 334 provides less material that needs to be compressed or clamped in the applicator 310. Compressing or clamping the applicator 310 allows the user to block the first fluid pathway 314 and/or the second fluid pathway 316 for testing.

FIG. 5 is a perspective view of a portion of the first layer 300 and the connector 332 of FIG. 3, illustrating additional details that may be associated with some embodiments. The connector 332 may comprise a first body 500 and a second body 502. In some embodiments, the first body 500 and the second body 502 may have a cylindrical shape. In some embodiments, the first body 500 and the second body 502 may have one or more flat surfaces. For example, the first body 500 and the second body 502 may have a rounded surface and a flat surface on an opposite side of the first body 500 and the second body 502 from the rounded surface. The flat surfaces of the first body 500 and the second body 502 may be configured to be coupled to the first surface 304 of the first layer 300. In some embodiments, the first body 500 and the second body 502 may each have a length. For example, the length of the first body 500 may be between about 7 and about 10 mm and the length of the second body 502 may be between about 5 and about 10 mm. In some embodiments, the length of the first body 500 and the second body 502 may be substantially equal. In other embodiments, the length of the first body 500 and the second body 502 may be unequal. For example, the length of the second body 502 may be greater than the length of the first body 500. In still other embodiments, the length of the first body 500 may be greater than the length of the second body 502.

In some embodiments, the first body 500 and the second body 502 of the connector 332 may each have a height. For example, the height of the first body 500 may be between about 6 and about 10 mm and the height of the second body 502 may be about 0.25 mm lesser than or greater than the thickness 308 of the first layer 300. In some embodiments, the height of the first body 500 and the second body 502 may be unequal. For example, the height of the first body 500 may be greater than the height of the second body 502. In other embodiments, the height of the first body 500 and the second body 502 may be substantially equal. In some embodiment, the height of one or both of the first body 500 and the second body 502 may be substantially equal to the thickness 308 of the first layer 300.

In some embodiments, the connector 332 may comprise a primary lumen, such as a first fluid path 508, and a secondary lumen, such as a second fluid path 510. The first fluid path 508 may be fluidly isolated from the second fluid path 510. In some embodiments, the connector 332 may fluidly isolate the first fluid pathway 314 from the second fluid pathway 316. For example, the first fluid path 508 may be fluidly coupled to the first fluid pathway 314 and the second fluid path 510 may be fluidly coupled to the second fluid pathway 316.

In some embodiments, the first body 500 may comprise a first end 504 and a second end 506. The first end 504 of the first body 500 may be configured to receive the conduit 220. In some embodiments, the first body 500 and the second body 502 may be a single device forming the connector 332. In other embodiments, the first body 500 and the second body 502 may be separate components coupled together to form the connector 332. For example, the second end 506 of the first body 500 may be configured to receive the second body 502. In some embodiments, the connector 332 may be formed by injection molding or machining.

Figure 6:
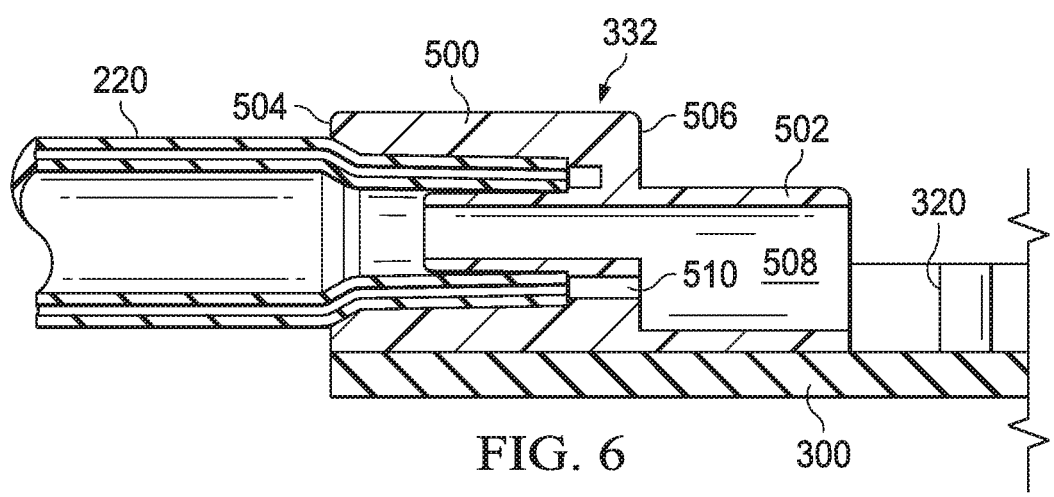
FIG. 6 is a cross-sectional view taken of the connector along line 6-6 in FIG. 5, illustrating additional details that may be associated with some embodiments.

FIG. 6 is a cross-sectional view taken of the connector 332 along line 6-6 in FIG. 5, illustrating additional details that may be associated with some embodiments. In some embodiments, the first fluid path 508 may extend from the first end 504 to the second end 506 of the first body 500 and through the second body 502 of the connector 332. The second fluid path 510 may extend from the first end 504 to the second end 506 of the first body 500. In some embodiments, the second fluid path 510 may be fluidly isolated from the first fluid path 508 and outbound of the first fluid path 508. For example, the second fluid path 510 may include one or more lumens surrounding the first fluid path 508.

In some embodiments, the conduit 220 may be a multi-lumen conduit fluidly coupled to the connector 332. For example, the conduit 220 may include a central lumen and one or more peripheral lumens surrounding the central lumen. In some embodiments, the central lumen may be fluidly coupled to the first fluid path 508 and the one or more peripheral lumens may be fluidly coupled to the second fluid path 510. In some embodiments, the central lumen of the multi-lumen conduit may comprise a negative-pressure delivery lumen, such as the negative-pressure delivery conduit 130, and the one or more peripheral lumens of the multi-lumen conduit may comprise a pressure sensing lumen, such as the pressure sensing conduit 134. In some embodiments, the negative-pressure delivery conduit 130 may be fluidly coupled to the first fluid path 508 of the connector 332 and the pressure-sensing conduit 134 may be fluidly coupled to the second fluid path 510 of the connector 332. The negative-pressure delivery conduit 130 may be configured to deliver negative pressure to the tissue site 202 and the pressure-sensing conduit 134 may be configured to sense negative pressure at the tissue site 202.

Figure 7:
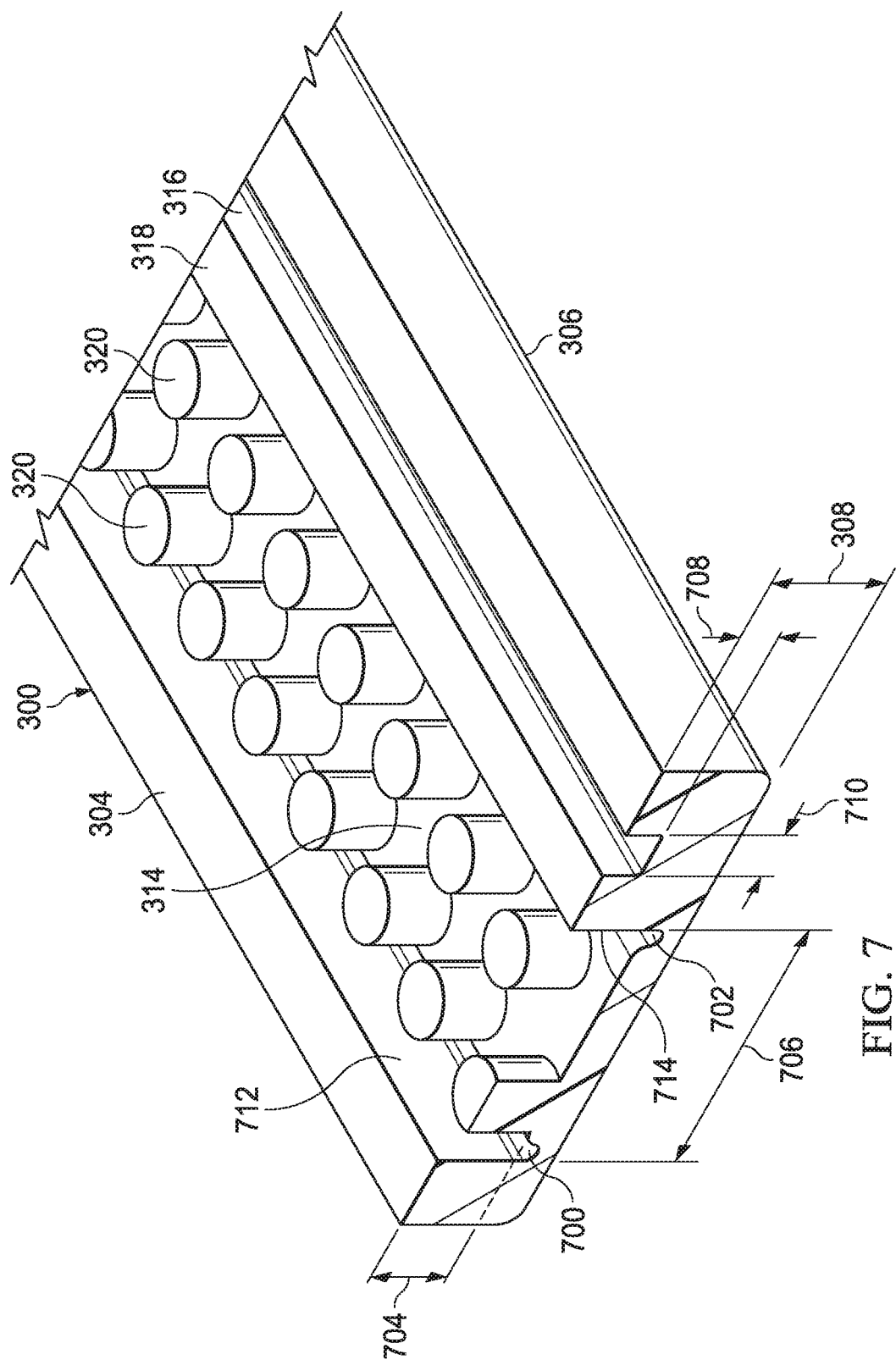
FIG. 7 is a cross-sectional perspective view taken of a portion of the first layer along line 7-7 of FIG. 3, illustrating additional details that may be associated with some embodiments.

FIG. 7 is a cross-sectional perspective view taken of a portion of the first layer 300 along line 7-7 of FIG. 3, illustrating additional details that may be associated with some embodiments. In some embodiments, the first fluid pathway 314 may comprise a first channel depth 704 extending into the thickness 308 of the first layer 300 from the first surface 304 toward the second surface 306. The first fluid pathway 314 may also have a first channel width 706 extending perpendicular to the first channel depth 704. In some embodiments, the first channel depth 704 may be between about 3 mm and about 5 mm, and the first channel width 706 may be between about 3 mm and about 5 mm.

In some embodiments, the second fluid pathway 316 may comprise a second channel depth 708 extending into the thickness 308 of the first layer 300 from the first surface 304 toward the second surface 306. The second fluid pathway 316 may also have a second channel width 710 extending perpendicular to the second channel depth 708. In some embodiments, the second channel depth 708 may be between about 3 mm and about 5 mm, and the second channel width 710 may be between about 3 mm and about 5 mm.

In some embodiments, the first layer 300 may comprise at least one gutter extending along the length of the first layer 300 and outbound of the first fluid pathway 314. For example, the first layer 300 may include a first gutter 700 extending along a first side 712 of the first fluid pathway 314 and a second gutter 702 extending along a second side 714 opposite the first side 712 of the first fluid pathway 314. The second side 714 of the first fluid pathway 314 may be adjacent the wall 318. In some embodiments, the first gutter 700 and the second gutter 702 may each extend along the length of the first layer 300 and parallel to the first fluid pathway 314. In other embodiments, the first layer 300 may also comprise a third gutter outbound of the second fluid pathway 316 and extending along the length of the first layer 300.

In some embodiments, the first gutter 700 and the second gutter 702 may prevent occlusion by keeping the first fluid pathway 314 open when the dressing interface 120 is under compression or tightly folded. For example, the first gutter 700 and the second gutter 702 may each have a width and a depth that resists blockages. The depth of the first gutter 700 and the second gutter 702 may extend from the first surface 304 into the thickness 308 of the first layer 300. In some embodiments, the depth of the first gutter 700 and the second gutter 702 may be greater than the first channel depth 704. For example, the depth of the first gutter 700 and the depth of the second gutter 702 may be between about 1 mm and about 2 mm deeper than the first channel depth 704. In some embodiments, the depth of the first gutter 700 and the second gutter 702 may be substantially equal. In other embodiments, the depth of the first gutter 700 and the depth of the second gutter 702 may be unequal. For example, the depth of the first gutter 700 may be greater than the depth of the second gutter 702 or the depth of the second gutter 702 may be greater than the depth of the first gutter 700.

The width of the first gutter 700 and the second gutter 702 may extend perpendicular to the depth of the first gutter 700 and the second gutter 702. In some embodiments, the width of the first gutter 700 and the second gutter 702 may be between about 1.5 mm to about 2 mm. In some embodiments, the width of the first gutter 700 and the second gutter 702 may be substantially equal. In other embodiments, the width of the first gutter 700 and the second gutter 702 may be unequal. For example, the width of the first gutter 700 may be greater than the width of the second gutter 702 or the width of the second gutter 702 may be greater than the width of the first gutter 700.

In operation, negative pressure may be supplied to the tissue site 202 by the dressing interface 120. Negative pressure supplied from the negative-pressure source 102 of the therapy unit 200 may travel through the conduit 220 to the dressing interface 120 for delivery to the tissue site 202, as shown in FIG. 2. In some embodiments, the conduit 220 may be a multi-lumen conduit comprising the negative-pressure delivery conduit 130 and the pressure-sensing conduit 134. In such embodiments, negative pressure supplied from the negative-pressure source 102 of the therapy unit 200 may travel through the conduit 220 to the connector 332. The connector 332 may separate the negative-pressure delivery conduit 130 from the pressure-sensing conduit 134. In some embodiments, the connector 332 may also fluidly couple the negative-pressure delivery conduit 130 to the first fluid pathway 314 and fluidly couple the pressure-sensing conduit 134 to the second fluid pathway 316. Negative pressure may then be supplied to the tissue site 202 through the negative-pressure delivery conduit 130 of the conduit 220, the first fluid pathway 314, and the first aperture 324 in the opening 322 of the applicator 310.

Pressure may also be measured at the tissue site 202 by the dressing interface 120. In some embodiments, the therapy unit 200 may include sensors for monitoring pressure at the tissue site 202. In some embodiments, the sensors may be fluidly coupled to the tissue site 202 via the pressure-sensing conduit 134 of the conduit 220. In such embodiments, the connector 332 may separate the pressure-sensing conduit 134 from the negative-pressure delivery conduit 130 and fluidly couple the pressure-sensing conduit 134 to the second fluid pathway 316 of the dressing interface 120. Pressure may then be sensed at the tissue site 202 through the pressure-sensing conduit 134 of the conduit 220, the second fluid pathway 316, and the second aperture 326 in the opening 322 of the applicator 310.

In other embodiments, instillation fluid may be delivered to the tissue site 202 through the second fluid pathway 316 of the dressing interface 120. For example, instillation fluid may be supplied from the solution source 118 of the therapy unit 200 and may travel through the conduit 220 to the second fluid pathway 316 of the dressing interface 120 for delivery to the tissue site 202. The instillation fluid and other fluids, such as wound exudate, may be removed by the negative-pressure source 102 of the therapy unit 200 through the first fluid pathway 314 of the dressing interface 120. In some embodiments, instillation fluid and other fluids may be collected in the container 106 of the therapy unit 200.

Figure 8:
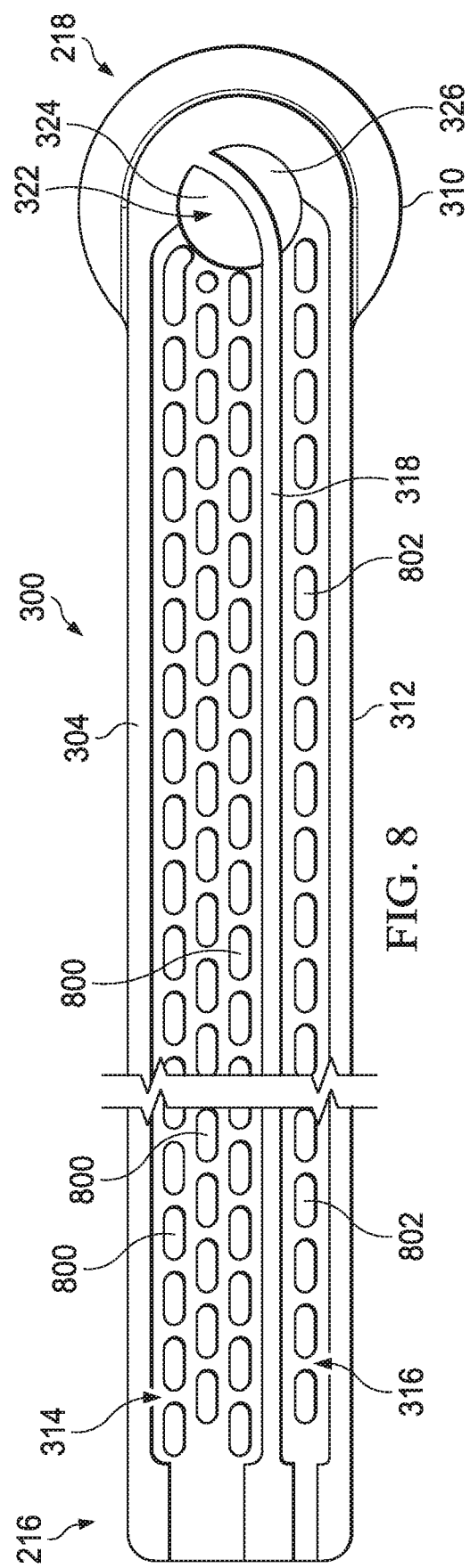
FIG. 8 is a plan view of another example of the first layer that may be associated with some embodiments of the dressing interface of FIG. 3.

FIG. 8 is a plan view of another example of the first layer 300 that may be associated with some embodiments of the dressing interface 120 of FIG. 3. In some embodiments, the first layer 300 may comprise a first plurality of features 800 projecting into the first fluid pathway 314 and a second plurality of features 802 projecting into the second fluid pathway 316. In some embodiments, the first plurality of features 800 and the second plurality of features 802 may have an ovoid shape. In other embodiments, the first plurality of features 800 and the second plurality of feature 802 may have a volumetric shape that is any one of a hemispherical, conical, cylindrical, rectangular, or geodesic shape.

In some embodiments, the first fluid pathway 314 and the second fluid pathway 316 may be fluidly isolated by the wall 318 and require separate connectors. For example, a first connector and a second connector (not shown) may be coupled to the first fluid pathway 314 and the second fluid pathway 316, respectively. The first connector and the second connector may be configured to fluidly couple the first fluid pathway 314 and the second fluid pathway 316 to the therapy unit 200.

In some embodiments, the wall 318 of the first layer 300 may extend into the applicator 310 and through the opening 322. For example, the wall 318 may extend into the opening 322 and divide the opening 322 into the first aperture 324 and the second aperture 326. In some embodiments, the first aperture 324 and the second aperture 326 may be substantially the same size. In other embodiments, the first aperture 324 may be larger than the second aperture 326. The size and position of the first aperture 324 and the second aperture 326 aids with fluidly coupling both the first fluid pathway 314 and the second fluid pathway 316 to the tissue site 202 even if the applicator 310 is misaligned with the hole 214 in the cover 110.

In some embodiments, the applicator 310 of FIG. 8 may be flexible and conform to contours of the tissue site 202. The flexibility and conformability of the applicator 310 may aid the user and/or patient with proper placement of the applicator 310 at the tissue site 202. Additionally, the applicator 310 may resist flattening against the tissue site 202 or lifting away from the tissue site 202 when under negative pressure.

A method for manufacturing an apparatus for managing fluid from a tissue site is also disclosed. In an example embodiment, the method may comprise providing a first layer and providing a second layer. The first layer may comprise a foam having a first surface and a second surface opposite the first surface. In some embodiments, the foam may comprise a closed-cell foam. In some embodiments, the foam may have a density of about 4 lb/ft$^3$ to about 20 lb/ft$^3$. The second layer may comprise a polymeric film having an outer surface and an inner surface. In some embodiments, the polymeric film may comprise ethylene vinyl acetate. In some embodiments, the polymeric film hay have a thickness between about 100 µm to about 250 µm.

The method may further comprise forming a first fluid channel on the first surface of the first layer, forming a second fluid channel on the first surface of the first layer, and forming a barrier on the first surface of the first layer. The barrier may be configured to fluidly isolate the first fluid channel from the second fluid channel Forming a first fluid channel may comprise thermoforming or laser etching the first fluid channel on the first surface of the first layer. Forming a second fluid channel may comprise thermoforming or laser etching the second fluid channel on the first surface of the first layer. The method may further comprise forming a first gutter outboard of the first fluid channel and forming a second gutter outboard of the first fluid channel opposite the first gutter. In some embodiments, the method may further comprise forming a third gutter outboard of the second fluid channel Forming the first gutter, the second gutter, and the third gutter may comprise thermoforming or laser etching the first surface of the first layer.

In some embodiments, the first fluid channel may comprise a plurality of features extending from the first surface of the first layer into the first fluid channel. In some embodiments, the plurality of features may be formed by pressing a heated tool into the first layer. For example, the plurality of features may be formed by pressing a heated steel tool into the first layer with a hydraulic press. In some embodiments, the plurality of features may comprise a first plurality of features, and the method may further comprises forming a second plurality of features on the first surface of the first layer extending into the second fluid channel.

In some embodiments, the method may further comprise disposing a first aperture in the first layer and disposing a second aperture in the first layer. The first aperture may be configured to be fluidly coupled to the first fluid channel, and the second aperture may be configured to be fluidly coupled to the second fluid channel. The method may further comprise coupling the inner surface of the second layer to the first surface of the first layer. For example, the inner surface of the second layer may be coupled to the first surface of the first layer by welding (RF or ultrasonic), heat sealing, or adhesive bonding such as, for example, acrylics or cured adhesives. In some embodiments, the method may also comprise, fluidly coupling at least one conduit to the first fluid channel and the second fluid channel.

In some additional embodiments, the method may further comprise providing a connector. Providing a connector may comprise coupling the connector to the first layer and the second layer. In some embodiments, coupling the connector may comprise ultrasonically welding the connector to the first layer and the second layer, thermally bonding the connector to the first layer and the second layer, or solvent bonding the connector to the first layer and the second layer. In some embodiments, coupling the connector may comprise bonding the connector to the first layer and the second layer. For example, the connector may be bonded to the first layer and the second layer by an adhesive. In some embodiments, the adhesive may be an ultra-violet, curable adhesive; a pressure-sensitive adhesive; or an epoxy. In some embodiments, the connector may be embedded in the first layer. The method may further comprise fluidly coupling the at least one conduit to the connector. The connector may fluidly isolate the first fluid channel from the second fluid channel.

The systems, apparatuses, and methods described herein may provide significant advantages. For example, the embodiments described herein may provide a dressing interface 120 that fluidly isolates the first fluid pathway 314 from the second fluid pathway 316, allowing negative-pressure delivery and pressure sensing to be separated. Additionally, this arrangement allows the first fluid pathway 314 and the second fluid pathway 316 to be leak tested individually. For example, the applicator 310 of the dressing interface 120 may be clamped and negative pressure or positive pressure delivered through the connector 332 and the dressing interface 120 to determine whether a leak exists in the first fluid pathway 314 or the second fluid pathway 316. The ability to detect a leak or blockage can reduce treatment maintenance, reduce ongoing therapy support time, and reduce replacement of devices and disposables.

Some embodiments described herein may be configured to simplify accurate placement of the dressing interface 120 at the tissue site 202. For example, the dressing interface 120 can decrease complications caused by misalignment of the dressing interface 120 with the hole 214 of the cover 110. The wall 318 may extend into the opening 322 of the applicator 310 and divide the opening into a first portion, such as the first aperture 324, and a second portion, such as the second aperture 326. The wall may wrap at least partially around the first aperture 324 of the opening 322. The first fluid pathway 314 may be fluidly coupled to first aperture 324 and the second fluid pathway 316 may be fluidly coupled to the second aperture 326. The second aperture 326 may surround at least a portion of the first aperture 324, ensuring that the first fluid pathway 314 and the second fluid pathway 316 are each fluidly coupled to the tissue site 202 through the opening 322 of the applicator 310, even if the applicator 310 is not centered on the hole 214 of the cover 110.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 104, the container 106, or both may be eliminated or separated from other components for manufacture or sale. In other example configurations, the controller 112 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for managing fluid from a tissue site, comprising:
   a first layer having a first end, a second end, a first surface, a second surface, and a thickness between the first surface and the second surface, the first layer comprising a foam;

a first fluid pathway disposed in the first surface of the first layer and extending from the first end to the second end;
a second fluid pathway disposed in the first surface of the first layer and extending from the first end to the second end;
a second layer having a first end, a second end, a first surface, and a second surface, wherein the second surface of the second layer is coupled to the first surface of the first layer; and
at least one gutter extending along a length of the first layer and outbound of the first fluid pathway, the at least one gutter having a depth extending into the thickness of the first layer and a width extending perpendicular to the depth.

2. The apparatus of claim 1, wherein the first fluid pathway comprises a first channel depth extending into the thickness of the first layer and a first channel width extending perpendicular to the first channel depth.

3. The apparatus of claim 1, wherein the second fluid pathway comprises a second channel depth extending into the thickness of the first layer and a second channel width extending perpendicular to the second channel depth.

4. The apparatus of claim 1, further comprising a wall extending from the first end to the second end of the first layer, the wall fluidly isolating the first fluid pathway and the second fluid pathway.

5. The apparatus of claim 1, wherein:
the first fluid pathway comprises a plurality of features projecting into the first fluid pathway;
the plurality of features have a volumetric shape that is any one of a hemispherical, conical, cylindrical, rectangular, or geodesic shape; and
the plurality of features are offset from each other.

6. The apparatus of claim 1, wherein:
the first fluid pathway comprises a first plurality of features projecting into the first fluid pathway and the second fluid pathway comprises a second plurality of features projecting into the second fluid pathway;
the first plurality of features and the second plurality of features have a volumetric shape that is any one of a hemispherical, conical, cylindrical, rectangular, or geodesic shape;
the first plurality of features are offset from each other; and
the second plurality of features are offset from each other.

7. The apparatus of claim 1, wherein the second end of the first layer comprises an applicator configured to be fluidly coupled to a tissue interface.

8. The apparatus of claim 7, further comprising a release layer removably coupled to the applicator.

9. The apparatus of claim 7, wherein the applicator comprises at least one aperture fluidly coupled to the first fluid pathway and the second fluid pathway.

10. The apparatus of claim 7, wherein:
the applicator comprises a first aperture fluidly coupled to the first fluid pathway and a second aperture fluidly coupled to the second fluid pathway;
the applicator comprises at least one opening in the second surface of the first layer;
the at least one opening is circular, and the first aperture comprises a first portion of the opening and the second aperture comprises a second portion of the opening; and
the second portion comprises a portion of a perimeter of the opening.

11. The apparatus of claim 10, further comprising:
a wall extending from the first end to the second end of the first layer, the wall fluidly isolating the first fluid pathway from the second fluid pathway; and
wherein the wall extends into the applicator, the wall fluidly isolating the first aperture from the second aperture.

12. The apparatus of claim 10, wherein the second aperture is adjacent to a distal end of the first layer.

13. The apparatus of claim 10, wherein the first aperture is larger than the second aperture.

14. The apparatus of claim 1, wherein the at least one gutter comprises:
a first gutter extending along a length of the first layer and a second gutter extending along the length of the first layer, the first gutter outbound of the first fluid pathway and the second gutter outbound of the first fluid pathway opposite the first gutter; and
wherein the first gutter and the second gutter each have a depth extending into the thickness of the first layer and a width extending perpendicular to the depth.

15. The apparatus of claim 1, further comprising a connector coupled to the first end of the first layer and the first end of the second layer.

16. The apparatus of claim 15, wherein the connector comprises:
a first cylindrical body having a first end and a second end;
a second cylindrical body coupled to the first end of the first cylindrical body;
a first fluid path extending from the second end of the first cylindrical body through the second cylindrical body, the first fluid path configured to be fluidly coupled to the first fluid pathway; and
a second fluid path extending from the second end to the first end of the first cylindrical body, the second fluid path configured to be fluidly coupled to the second fluid pathway.

17. The apparatus of claim 15, wherein:
the connector fluidly isolates the first fluid pathway from the second fluid pathway;
the connector has a primary lumen fluidly coupled to the first fluid pathway and at least one secondary lumen fluidly coupled to the second fluid pathway; and
the connector is configured to receive a multi-lumen conduit and fluidly couple a delivery lumen of the multi-lumen conduit to the primary lumen and a sensing lumen of the multi-lumen conduit to the at least one secondary lumen.

18. The apparatus of claim 15, further comprising a conduit fluidly coupled to the connector.

19. The apparatus of claim 1, further comprising at least one aperture disposed in the second end of the first layer; wherein the first fluid pathway and the second fluid pathway are fluidly coupled to the at least one aperture.

* * * * *